(12) United States Patent
Ha et al.

(10) Patent No.: US 11,801,495 B2
(45) Date of Patent: *Oct. 31, 2023

(54) CATALYSTS COMPRISING SILICON MODIFIED NICKEL

(71) Applicant: WASHINGTON STATE UNIVERSITY, Pullman, WA (US)

(72) Inventors: Su Yun Ha, Pullman, WA (US); M. Grant Norton, Pullman, WA (US); Oscar Gerardo Marin Flores, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 25 days.

This patent is subject to a terminal disclaimer.

(21) Appl. No.: 17/319,361

(22) Filed: May 13, 2021

(65) Prior Publication Data

US 2021/0339230 A1 Nov. 4, 2021

Related U.S. Application Data

(63) Continuation of application No. 16/298,293, filed on Mar. 11, 2019, now Pat. No. 11,033,882.
(Continued)

(51) Int. Cl.
*B01J 23/755* (2006.01)
*B01J 35/00* (2006.01)
(Continued)

(52) U.S. Cl.
CPC .............. *B01J 23/755* (2013.01); *B01J 21/08* (2013.01); *B01J 35/002* (2013.01); *B01J 35/008* (2013.01);
(Continued)

(58) Field of Classification Search
CPC ........ B01J 21/08; B01J 23/755; B01J 35/008; B01J 35/0086
See application file for complete search history.

(56) References Cited

U.S. PATENT DOCUMENTS

2018/0353942 A1* 12/2018 Liang ..................... B01J 35/026

FOREIGN PATENT DOCUMENTS

| CN | 105964261 A | * | 9/2016 | ............ B01J 23/755 |
| CN | 108855095 A | * | 11/2018 | ............ B01J 23/755 |

OTHER PUBLICATIONS

Chen et al. (A simple and convenient approach for preparing core-shell-like silica@nickel species nanoparticles: highly efficient and stable catalyst for the dehydrogenation of 1,2-cyclohexanediol to catechol, Dalton Trans., 2015 vol. 44, p. 1023-1038).*
(Continued)

*Primary Examiner* — Jun Li
(74) *Attorney, Agent, or Firm* — WC&F IP

(57) ABSTRACT

Nickel-based catalysts comprising silicon modified nickel (nickel silicate) are provided, as are methods for using the catalysts to i) convert methane to CO and $H_2$ (e.g. for use in synthetic chemical compound production); or to ii) convert methane to oxygenated hydrocarbons e.g. one or more of methanol, acetone, formaldehyde, and dimethyl ether. The catalysts are bifunctional and comprise both Ni metallic catalytic sites and acidic nickel-silicon catalytic sites, and the conversions are performed under moderate reaction conditions.

2 Claims, 14 Drawing Sheets

Related U.S. Application Data

(60) Provisional application No. 62/641,526, filed on Mar. 12, 2018.

(51) Int. Cl.

| | |
|---|---|
| *B01J 35/02* | (2006.01) |
| *B01J 37/04* | (2006.01) |
| *B01J 37/10* | (2006.01) |
| *C01B 3/40* | (2006.01) |
| *C07C 29/151* | (2006.01) |
| *C07C 45/49* | (2006.01) |
| *C07C 41/01* | (2006.01) |
| *B01J 37/00* | (2006.01) |
| *B01J 21/08* | (2006.01) |

(52) U.S. Cl.
CPC ....... *B01J 35/0013* (2013.01); *B01J 35/0073* (2013.01); *B01J 35/023* (2013.01); *B01J 37/009* (2013.01); *B01J 37/04* (2013.01); *B01J 37/105* (2013.01); *C01B 3/40* (2013.01); *C07C 29/1518* (2013.01); *C07C 41/01* (2013.01); *C07C 45/49* (2013.01); *C01B 2203/0261* (2013.01); *C01B 2203/1058* (2013.01); *C01B 2203/1241* (2013.01)

(56) References Cited

OTHER PUBLICATIONS

Machine translation of Zhang et al. to CN105964261, publication date May 24, 2016.*

Machine translation of Li et al to CN 108855095, publication date Nov. 23, 2018.*

* cited by examiner

Figure 2A
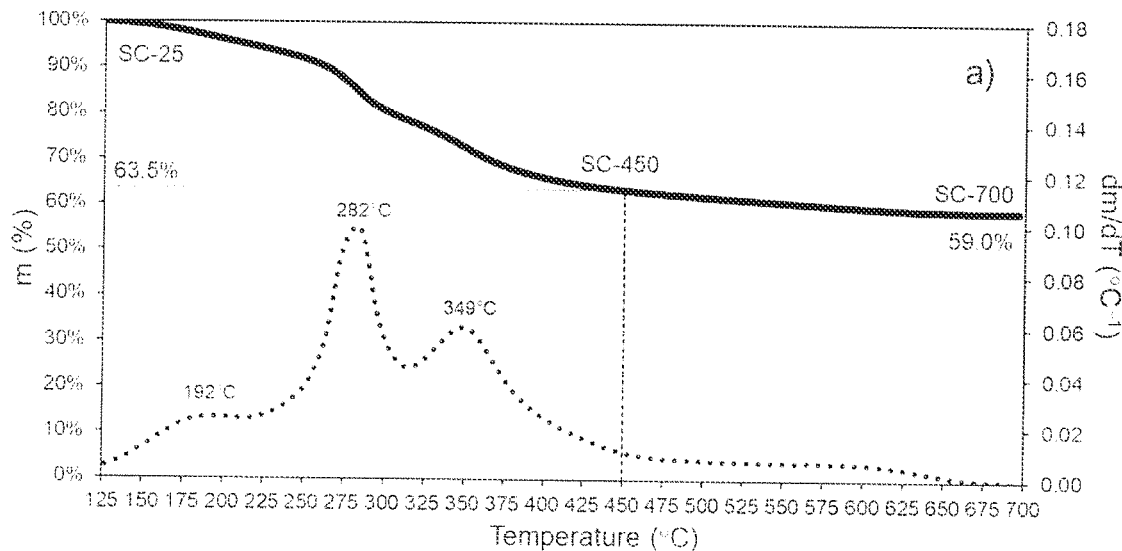
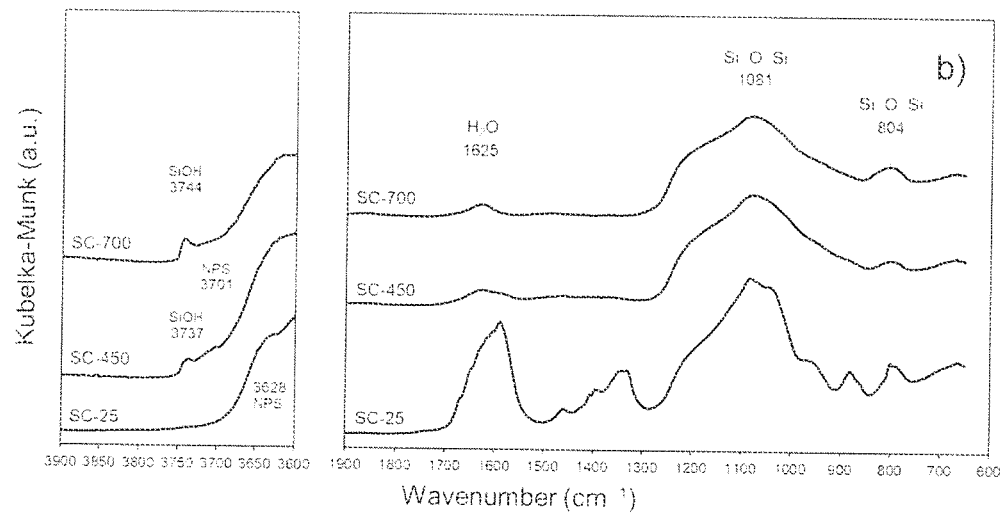
Figure 2B

CATALYSTS COMPRISING SILICON MODIFIED NICKEL

CROSS-REFERENCE TO RELATED APPLICATIONS

This application claims benefit of U.S. provisional patent application 62/641,526, filed Mar. 12, 2018.

FIELD OF INVENTION

The invention relates to nickel-based catalysts. In particular, the invention relates to catalysts comprising silicon modified nickel (nickel silicate) that are used, for example, to convert methane to oxygenated hydrocarbons under moderate conditions and in a single step.

BACKGROUND OF THE INVENTION

Efforts to use natural gas in transportation, either directly or by conversion to a liquid fuel, have been spurred by recent increases in available supply and a growing price spread between natural gas and petroleum, especially in the United States. Current natural gas-to-liquids (GTL) approaches generally operate on scales similar to those of petroleum refineries and suffer from low energy and carbon efficiencies, as well as high capital cost [1]. These plants are economically viable only for plants producing at least 30 thousand barrels per day (Mbpd) of liquid fuel. Unfortunately, small-scale methane sources are often flared or vented, which is wasteful and adds to greenhouse gas emissions.

Smaller, modular GTL plants are suitable for use in remote locations to capture small-scale methane sources. In contrast to conventional GTL plants, they are designed for the economical processing of smaller amounts of gas ranging from 100 to 1500 million cubic meters (MMcm) and producing e.g. 1,000 bpd-15,000 bpd of liquid fuels [2]. The plants are typically scaled to match the size of the resource, expanded as necessary, and can be integrated with existing facilities at refinery sites. Smaller-scale GTL operations also pose a lower risk to producers. Since the plants are smaller and modular, construction costs are reduced and investment can be phased.

There is a strong interest in developing compact GTL technologies. The GTL process used most frequently involves two main operations: conversion of natural gas into a syngas via steam methane reforming (SMR) or autothermal reforming (ATR), followed by Fischer-Tropsch (FT) synthesis to convert the syngas to a liquid, and small footprint technologies must integrate these processes [3].

A major hurdle is to make the syngas production unit economical on a small scale, as it comprises the majority (e.g. about 60%) of the capital cost, while the remaining 40% can be attributed to liquid synthesis. This is due at least in part to the use of steam reforming, which has a significant energy requirement (due to the strong endothermicity of the reforming reactions) and the high initial investments (the steam reforming section is responsible for 50-75% of the capital costs) [4].

The catalytic partial oxidation (CPO) process is an attractive alternative for converting methane to syngas because it avoids the need for large amounts of energy and works well in small reactors due to the faster oxidation reaction. In addition, in the CPO process, the $H_2/CO$ ratio in syngas products is 2:1, which allows straightforward syngas utilization for Fischer-Tropsch synthesis. Ni and a variety of noble metals (Ru, Rh, Pd, Ir, Pt) are typically used as the active phases for CPO in the methane reforming process [5-8]. For economic considerations, Ni is the most widely used; however, it has very high susceptibility to sintering which causes coke deposition with the subsequent deactivation of active sites. Thus, the lifetime of current Ni catalyst is severely limited, compared to noble metal catalysts. However, the latter are very expensive.

It would be advantageous to have available relatively inexpensive Ni catalysts with high catalytic capability and high stability (less susceptibility to coking) at low operating temperatures, e.g. stability comparable to that of noble metal catalysts.

SUMMARY OF THE INVENTION

The present disclosure provides novel Ni-based catalysts which are highly catalytically active and stable at low operating temperatures. The catalysts comprise silicon modified nickel and the active sites of the catalysts have the ability to catalyze the partial oxidation of methane at low temperatures. They are thus ideal for use in CPO reactions in small-scale GTL operations to produce products such as syngas components e.g. CO and $H_2$. CO and $H_2$ can then be converted into other useful products. For example, they can be converted to a liquid fuel via a Fischer-Tropsch (FT) reaction. In addition, by adjusting the reaction conditions, other useful oxygenated products can be made (e.g. dimethyl ether, acetone, formaldehyde and methanol).

The present disclosure provides a catalytic nanoparticle comprising an internal core comprising metallic nickel, and at least one external layer comprising Ni and SiOx species, wherein the at least one external layer surrounds the internal core. In some aspects, the Ni in the external layer exhibits an increase in the binding energy (BE) of about 2-3 eV, with respect to the Ni metallic state. In other aspects, the $\Delta BE$ of Ni with respect to its metallic state, ranges from 0.5 eV to less than 2 eV in the external layer, and the nanoparticles further comprises an intermediate layer between the internal core and the external layer, the intermediate layer comprising Ni and SiOx species with Ni exhibiting a BE that is less than 0.5 eV, with respect to the Ni metallic state. In further aspects, the catalytic nanoparticles have a mean particle size of from 2-5 nm. In additional aspects, the catalytic nanoparticle does not comprise a nickel oxide phase.

The disclosure also provides a catalyst preparation comprising a plurality of the nanoparticles.

The disclosure also provides a catalyst made by i) forming a mixture of nickel formate dihydrate and tetraethyl orthosilicate in an organic solvent; 2) hydrolyzing tetraethyl orthosilicate in the mixture to form a gel comprising phyllosilicate sheets with nickel precursor in the interlayer space; 3) drying the gel; 4) forming the dried gel into nanoparticles; and 5) heating the nanoparticles to a temperature sufficient to anneal at least a portion of the nickel and the phyllosilicate sheets, and to activate metallic nickel reactive sites and nickel-silicon acidic reactive sites in the nanoparticles. In some aspects, the organic solvent is ethylene glycol (EG). In other aspects, the step of hydrolyzing is performed by adding $H_2O$ to the mixture. In further aspects, the step of heating is performed under a flowing inert gas. In yet further aspects, the temperature is at least 200° C.

Also provided is a method of producing synthetic chemical compounds, comprising contacting methane with the catalyst preparation, thereby forming CO and $H_2$; and reacting the CO and $H_2$ via a Fischer-Tropsch (FT) synthesis to produce the synthetic chemical compounds.

Also provided is a method of producing oxygenates from methane, comprising converting the methane with the catalyst preparation; and collecting the oxygenates produced in the step of converting. In some aspects, the step of converting is performed in the presence of air at a temperature between 200-450° C. In other aspects, the oxygenates include at least one of methanol, acetone, formaldehyde, and dimethyl ether.

BRIEF DESCRIPTION OF THE FIGURES

FIGS. 2A and B. Characterization of catalyst samples: A, thermogravimetric analysis, B, analysis using infrared (IR) spectroscopy using diffuse reflectance (DRIFTS).

DETAILED DESCRIPTION OF THE INVENTION

Figure 1:
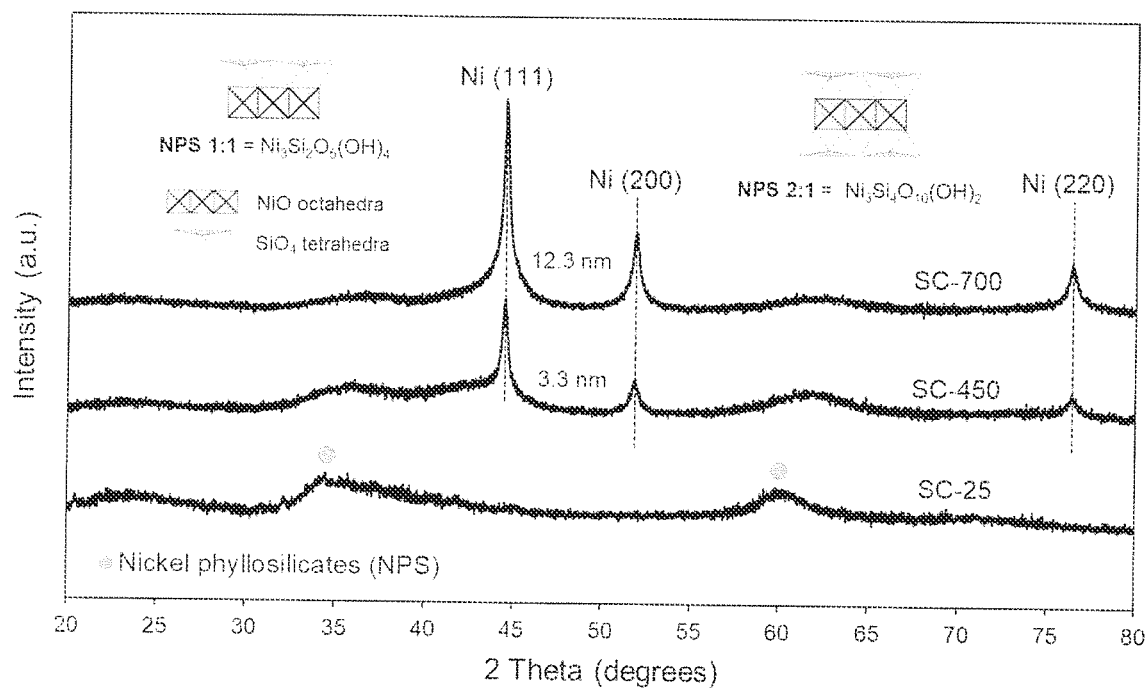
FIG. 1. Diffractograms of samples described in the Examples.

The detailed description set forth below is intended as a description of exemplary embodiments of the invention and is not intended to represent the only forms in which the present invention may be constructed or utilized. The description sets forth the functions and the sequence for constructing and operating the invention. It is to be understood, however, that the same or equivalent functions and sequences may be accomplished by different embodiments that are also intended to be encompassed within the spirit and scope of the invention.

The disclosure provides novel processes to synthesize a silica-supported nickel catalyst with high loading and exceptional dispersion.

The catalyst does not require $H_2$ pretreatment to become active for $CH_4$ oxidation. The catalyst cracks $CH_4$ to produce carbon and hydrogen at temperatures of 300° C. and higher.

The catalyst activates $CH_4$ at temperatures as low as 200° C. in the presence of air. The catalyst processes more than 1 $m^3$ $CH_4$/day-Kg cat., and produces more than 150 Kg/day-Kg cat. of oxygenated compounds, for example, dimethyl ether, acetone, formaldehyde and methanol.

Definitions

Syngas, or synthesis gas, is a fuel gas mixture consisting primarily of hydrogen, carbon monoxide, and very often some carbon dioxide. The name comes from its use as an intermediate in creating synthetic chemical compounds. Syngas is also combustible and is used e.g. as a fuel in internal combustion engines.

Phyllosilicates, or sheet silicates, form parallel sheets of silicate tetrahedra with $Si_2O_5$ i.e. a 2:5 ratio of Si to O. All phyllosilicate minerals are hydrated, with either water or hydroxyl groups attached.

Nickel (II) oxide is the chemical compound with the formula NiO. NiO adopts the "rock salt" (NaCl) structure, with octahedral $Ni^{2+}$ and $O^{2-}$ sites ("octahedral NiO"). NiO is often non-stoichiometric, deviating from a 1:1 Ni:O composition.

Photoelectron: an electron emitted from an atom by interaction with a photon, especially an electron emitted from a solid surface by the action of light. The energy required to eject a given electron from the atom is known as the binding energy.

Novel Ni-based catalysts comprising silicon modified nickel are described herein. The catalysts are advantageously highly active and resistant to sintering, which is a problem with prior art Ni catalysts. Significantly, the active sites of the catalysts display high catalytic activity and readily catalyze the partial oxidation of methane at low temperatures in the presence of molecular oxygen. They are thus ideal for use in CPO reactions to convert methane to oxygenated products, for example to convert methane to syngas in small-scale GTL operations. Methods for converting methane to oxygenated products using the catalysts are also encompassed herein, as are systems which comprise the catalyst. In some aspects, the systems are or are included in GTL operations. In other aspects, products such as dimethyl ether (DME), acetone, formaldehyde, methanol are formed.

Catalyst Preparation

Preparation of the catalysts involves reacting starting materials that include a Ni (Ni containing) precursor and a silica (silica containing) precursor. Suitable Ni precursors include but are not limited to: nickel formate dihydrate, nickel nitrate hexahydrate, nickel acetate tetrahydrate, and nickel acetylacetonate. In preferred aspects, the Ni precursor is nickel (II) formate dihydrate, $Ni(HCO_2)_2 \cdot 2H_2O$. A benefit of using nickel formate dihydrate is that this precursor can be directly converted to metallic nickel upon heating under inert environments.

Suitable silica ($SiO_2$) precursors include but are not limited to: tetraethyl orthosilicate (TEOS), and tetraethylsilane. In preferred aspects, the silica precursor is TEOS ($Si(OC_2H_5)_4$), also known as orthosilicic acid tetraethyl ester, silicon tetraethoxide, tetraethoxysilane, tetraethoxysilicon(IV), tetraethyl silicate, etc.

To form a catalyst, the Ni precursor and the Si precursor are dissolved in a suitable solvent, e.g. by dissolving the Ni precursor in the solvent and then adding the Si precursor, or vice versa, or even adding the two precursors simultaneously. Dissolution typically is carried out at an elevated temperature, e.g. at least about 70, 75, 80, 85, 90, 95 or even 100° C., such as about 90° C. Dissolution takes place (e.g. with agitation such as stirring) for a period of time ranging from about 30 minutes to about 4 hours, such as for about 1, 2 or 3 hours, as needed.

Next, the Si precursor is decomposed/hydrolyzed, e.g. using a sol-gel process by adding to the mixture a volume of water in excess of the volume of Si precursor. In some aspects, the volume of water that is added is about 1-10, e.g. about 5 times that of the Si precursor. Hydrolysis is allowed to proceed at a temperature e.g. at least about 70, 75, 80, 85, 90, 95 or even 100° C., such as about 90° C., for a period of time ranging from about 1-10 hours, such as for about 5 h. Thereafter, the reaction mixture is cooled e.g. to room temperature without agitation, resulting in formation of a gel comprising e.g. nickel phyllosilicate layered structures with unreacted nickel precursor in the interlayer space.

Water is removed from the gel, e.g. by centrifugation, drying, etc. For example, the gel may be dried a temperature e.g. at least about 70, 75, 80, 85, 90, 95 or even 100° C. for a period of time ranging from about 1-2 days to one week, such as about 3 days. The resulting solid is (optionally) ground (pulverized) to fine particles using, e.g. a mortar and pestle until the particle size lies within the micron range.

In order to obtain the metallic nickel nanoparticles that constitute the catalyst, the dried gel is or the dried gel particles are exposed to at least one high temperature to affect annealing. Annealing may occur at a single temperature, or may be carried out at two or more temperatures e.g. begun at a first temperature and completed at a second (or even a second and third temperature), etc. The selection of a temperature and a time of annealing depend on the degree of annealing that is desired, and different temperatures and times result in the formation of catalysts with differing properties. Thus, lower annealing temperatures (200-300° C.) appear to favor the acidic features while higher temperatures (300-450° C.) enhance the formation of metallic sites at the expense of the acidic sites. This makes it possible to expand the range of potential applications for these catalytic materials. Elevated temperatures (>450° C.) may lead to silica-supported metallic nickel nanoparticles, which in general are not as active as the samples obtained using lower annealing temperatures, but which may be suitable for selected reactions.

In some aspects, the temperature is in the range of from about 200-700° C., e.g. at about 200, 250, 300, 350, 400, 450, 500, 550, 600, 650, or 700° C.

The annealed mixture is typically held at the elevated temperature (or at more than one elevated temperature) for from about 15 minutes to about 2 hours or longer e.g. about 15, 30, 45 or 60 minutes, such as about 30 min., or about 1, 1.5 or 2 hours, or longer as needed to achieve the desired catalyst properties.

Annealing is generally performed under an inert gas (e.g. $N_2$, argon, or another suitable gas) using a suitable heating rate (e.g. about 1-10 K/min, such as about 5 K/min) starting at room temperature (taken to be about 25° C.).

The addition of hydrogen is not required at any stage of the catalyst preparation process. However, without being bound by theory, it is believed that the collapse of the phyllosilicate structures to form Ni-silicate as described herein was likely accelerated by the presence $H_2$ produced during the decomposition of the nickel precursor.

Further, the methods described herein do not require acids or bases as catalysts. This is in contrast to prior art sol-gel approaches, which usually involve the use of acids or bases as catalysts to accelerate the polymerization of the silicon-containing species. However, the use of acids or bases in reactions to form the catalysts is not precluded, i.e. they may be included in some aspects.

The Catalysts

The resulting catalytic material comprises nanoparticles having both a metallic nickel phase and at least one nickel-silicate phase. In general, the metallic nickel phase comprises nickel crystallite (regions of largely regular crystalline Ni structure) that is located at and makes up the central core of the nanoparticle. At least one nickel-silicate phase generally surrounds the central metallic Ni core, forming a layer (or layers) adjacent to and outside the core, e.g. see FIGS. 3E and 3F. If only one external layer is present, generally the Ni and SiOx "interact strongly" producing a loss of metallic character by the nickel atoms in this layer that can be inferred from the increase in the binding energy ($\Delta BE$) of Ni photoelectrons of ~2-3 eV (compared to that of metallic Ni when measured under the same conditions) If two layers are present outside the internal core, in the outermost external layer, the Ni and SiOx "interact mildly" (0.5 eV<$\Delta BE$<2 eV) and in the other layer, which is located in between the core and the outmost external layer, the Ni and SiOx "interact weakly" ($\Delta BE$<0.5 eV).

The nanoparticle size generally ranges from about 2 to about 20 nm, such as about 2, 4, 6, 8, 10, 12, 14, 16, 18, 19 or 20 nm, and is typically in the range of from about 2-10 nm, e.g. about 2, 3, 4, 5, 6, 7, 8, 9, or 10 nm.

The catalysts exhibit excellent dispersion of the metallic nickel phase, and thus contain accessible sites at which Ni acts as a catalyst; and the catalysts also contain a large number of acidic nickel-silicon sites on the surface of the nickel silicate phase. Thus, the catalysts are advantageously dual catalysts with both metallic and acidic reactive sites, which coexist on the catalyst surface. Although part of the metallic core may be exposed to the reaction mixture, it is believed that these Ni atoms are catalytically active only at high temperatures (>500° C.).

Without being bound by theory, it is believed that a synergistic effect (i.e. a bifunctional catalytic effect) between these two different types of sites is responsible for the activity exhibited by this material. In some aspects, different adsorption behaviors for reactants may lead to the formation of e.g. methyl groups ($CH_{3-}$) on the Ni metallic sites and e.g. mobile methoxy groups ($OCH_3$) on the Ni-SiOx acidic sites, which can combine on the surface of the catalyst and generate molecules such as dimethyl ether ($CH_3$—O—$CH_3$).

Reactions

The present disclosure encompasses methods for converting methane to oxygenated compounds via methane activation and partial oxidation. The methods include exposing methane to (contacting methane with) a nickel silicate catalyst material as described herein, in the presence of at least one oxidizing agent. Contact is made under conditions suitable for (conducive to) partially oxidizing the methane.

These reactions are conducted in the presence of an oxidizing agent. Suitable oxidizing agents include but are not limited to air, $CO_2$, $O_2$, $H_2O$, $H_2O_2$, $N_2O$, etc. and/or mixtures of these. For example, in some aspects, a mixture of air and $H_2O$ is used, Reactions can be performed at high space velocities (up to 4 L/min-g); however, typical experiments are usually carried out at space velocities of ~3-3.5 L/min-g. When a mixture of air and $H_2O$ is used as oxidizing agent, the $O_2$ to $CH_4$ molar ratio is 0.5 or lower while the steam to $CH_4$ molar ratio is 0.1 or higher. It is noted that in some aspects, the oxidizing agent is or includes $CO_2$ that is generated during the course of catalysis, i.e. $CO_2$ that is formed by partial oxidation of methane when exposed to the catalyst, and that then continues to react with methane.

In preferred aspects, the reactions are conducted under relatively mild or moderate conditions of pressure and temperature. By "moderate conditions of pressure" we mean a pressure ranging from 1 to 500 psi, e.g. about 1, 10, 50, 100, 150, 200, 250, 300, 350, 400, 450 or 500 psi. By "mild conditions of temperature" we mean that the reaction is generally performed at a temperature ranging from about 200° C. to about 450° C., such as at about 200, 225, 250, 275, 300, 325, 375, 400, 425, or 450° C.

As another embodiment, the activity and/or selectivity of the reactions described herein may be enhanced by using transition metals as promoters to modify the properties of the catalytic material. For example, the addition of copper may enhance the selectivity to methanol due to suppression of CO production. Similarly, the incorporation of alkali metals and alkaline earth metals may inhibit the formation of carbon deposits and promote the activation of water molecules, respectively. Suitable transition metals for catalytic activity enhancement include but are not limited to: molybdenum, manganese, iron, copper, cobalt, and lanthanum. Alkali/alkaline earth metals for the same purpose include but are not limited to Na, K, Ba, Mg, etc. In some aspects, the transitions metals are incorporated into the catalyst structure through impregnation of catalyst samples with a solution of the transition metal precursor, via the addition of the metal precursor during the synthesis procedure, or by engineering composite materials. Similarly, the introduction/incorporation of alumina or reducible oxides such as ceria may lead to changes in the catalytic material that can modify the catalyst activity and/or selectivity. For example, the addition of alumina may increase the acidity of the catalytic material, thus facilitating the activation of $CH_4$. Similarly, the incorporation of a reducible oxide such as ceria may change the mechanism of activation of $O_2$ to produce lattice oxygen $O^{2-}$, a weak oxidizing agent that may decrease the selectivity to $CO_2$. Also, the addition of steam into the reaction system as a reactant can produce changes in the activity and/or selectivity to selectively produces specific oxygenated compounds. For example, activated water may act as a source of the hydroxyl groups required to produce methanol or other oxygenated compounds. Thus, in some aspects, the activity and/or selectivity of the Ni-silica catalysts described herein are modified (e.g. increased or changed) by these measures. For example, in some aspects the catalysts are used so as to promote partial oxidation of methane to make $H_2$ and CO, and in other aspects, the catalysts are used to produce oxygenated compounds such as dimethyl ether (DME), acetone, formaldehyde, methanol, etc.

The particular features displayed by this catalytic material open mainly two possible routes to produce oxygenated compounds. The first one can be considered a direct route, where a reaction mixture comprising $CH_4$ and $O_2$ or other oxidizing agent produces oxygenated compounds with high selectivity. The second pathway involves the production of syngas as the initial step, and the conversion of syngas to oxygenated compounds by performing a Fischer-Tropsch synthesis as the final step. Although the second route involves two reaction steps, the fact that both reactions can be performed at similar operating conditions makes it possible to carry out the entire process in one single reactor, using our novel catalyst to produce syngas and a commercially available Fischer-Tropsch catalyst for the conversion of syngas to oxygenated compounds.

Products Produced

Products produced directly by contacting methane and an oxidizing agent with the catalyst described herein include $H_2$, CO and $CO_2$. In some aspects of the disclosure, the $H_2$ and CO are then further reacted e.g. via a Fischer-Tropsch (FT) reaction to form liquid hydrocarbons or oxygenated compounds, depending on the FT catalyst employed. Examples of such liquid hydrocarbons include but are not limited to straight-chain alkanes and alkenes. Oxygenated compounds may include methanol, ethanol, and higher alcohols, as well as dimethyl ether, formaldehyde, formic acid and others. With respect in particular to DME, the direct conversion of methane to dimethyl ether (DME) provides an environmentally friendly alternative fuel for e.g. diesel engines, either for transportation applications, and/or power generation.

Reactors and Systems

In some aspects, the catalyst described herein are incorporated into GTL systems. In these aspects, the systems typically also incorporate (or are incorporated into) a Fischer-Tropsch process reactor. An important requirement of the reactor for the Fischer-Tropsch process is removal of heat. Several styles of suitable reactors are known and may be used, including but not limited to slurry reactors, fluid-bed and circulating catalyst (riser) reactors, multi tubular fixed-bed reactors (also known as trickle flow reactors), entrained flow reactors, microchannel reactors, etc.

Figure 12A:
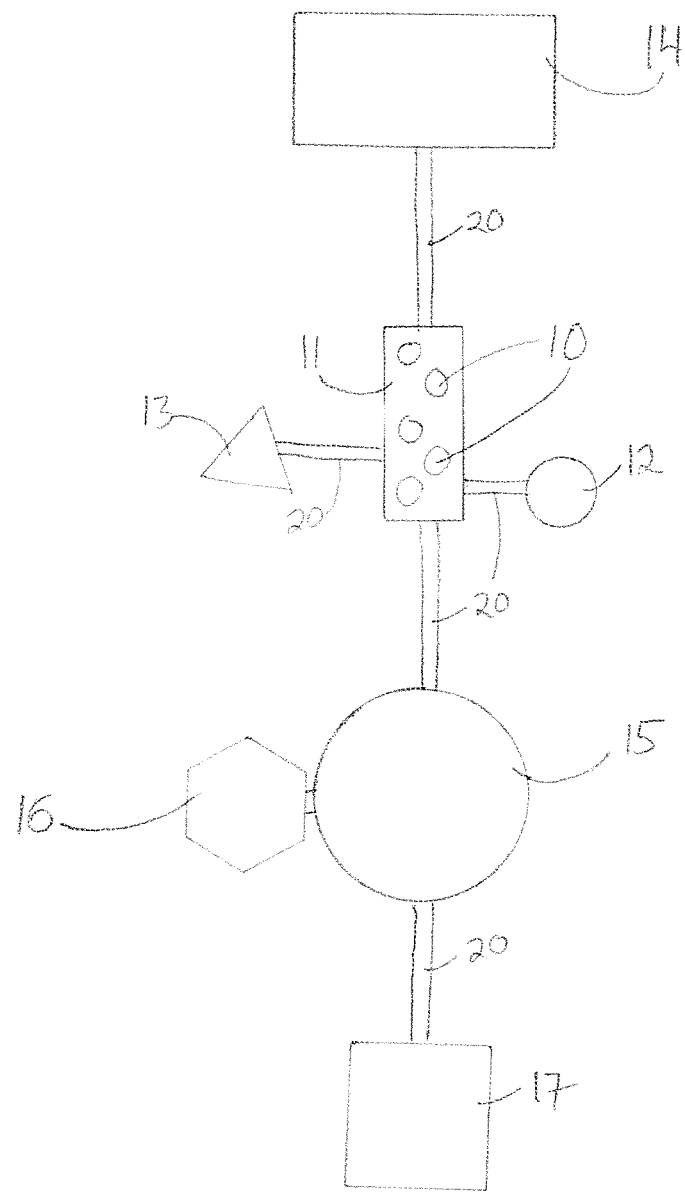
FIGS. 12A and B. Schematic representations of exemplary GTL systems having A, multiple reaction modules and B, a single reaction module.

Exemplary systems are schematically represented in FIGS. 12A and B. Shown in FIG. 12A are: catalyst particles 10 housed in container or first reaction module 11, which is configured to receive methane from methane source 14, an oxidizing agent from oxidizing agent source, 12, and to be heated via heating means 13. CO and $H_2$ produced in reaction module 11 are passed to second reaction module 15 where the Fischer-Tropsch reaction takes place. Second reaction module 15 may be cooled (to dissipate heat from the exothermic reaction) via cooling means 16. The products produced by the Fischer-Tropsch reaction are collected (an optionally further cooled or condensed) in collection means 17. Connecting lines 20 represent various tubes, channels, conduits, etc. through which the various reactants and products are transferred.

Figure 12B:
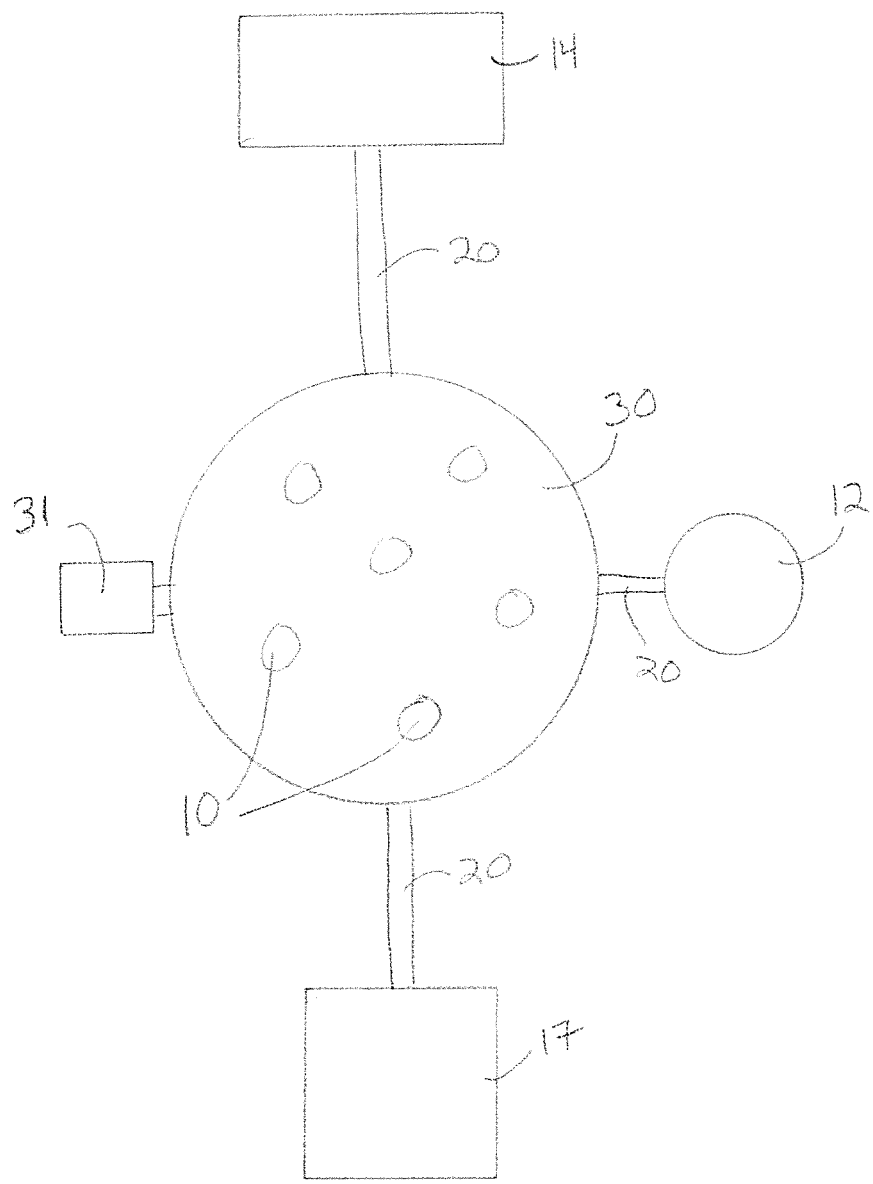

FIG. 12B depicts a second exemplary system in which only one reaction module (reaction module 30) is present. In this exemplary system, the catalyst particles 10 are mixed directly in with the components necessary to conduct the Fischer-Tropsch reaction in reaction module 30, and the heat generated by the exothermic Fischer-Tropsch serves to supply heat required for the reactions catalyzed by the catalyst. If necessary, temperature regulator 31 may be present (and operably connected to reaction module 30) to further heat or cool the reactants. The other components are as described above, with methane source 14 and oxidizing agent source 12 delivering methane and oxidizing agent, respectively, directly to reaction module 30.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Low Temperature Catalytic Partial Oxidation of Methane (LTCPOM) for Gas-to-Liquid Applications Over a Silicon-Modified Nickel Catalyst The traditional technology for syngas production is steam reforming. The main drawbacks of this technology for GTL applications are the significant energy requirement and the high initial investments. The catalytic partial oxidation (CPO) process is an attractive alternative because it avoids the need of large amounts of energy and requires smaller reactors due to the faster oxidation reaction.

For methane reforming processes, Ni is the most widely used active phase. However, it presents high susceptibility to sintering which causes coke deposition and, then, a deactivation of its active sites. The present work provides a solution to this problem by modifying a nickel catalyst with silicon to generate active sites with the ability to activate methane at low temperatures in presence of molecular oxygen, thereby lessening sintering and maintaining activations of the catalyst's active sites.

Methods

The chemicals utilized for the preparation of the catalytic materials were nickel formate dihydrate and tetraethyl orthosilicate (TEOS) as nickel (Ni) and silicon (Si) precursors, respectively. The catalyst preparation was performed using a sol-gel approach. Typically, the Ni precursor was initially dissolved in ethylene glycol (EG) at 90° C., and subsequently mixed with the Si precursor that was added under constant stirring for 2 h at the same temperature. Next, the silicon precursor was decomposed by adding a volume of nanopure water 5 times that of TEOS. The hydrolysis was carried out at 90° C. for 5 h, after which the resulting product was left overnight to cool down at room temperature without stirring. The resulting gel was subsequently centrifuged and dried at 90° C. for 3 days. The resulting solid was ground and then annealed under a flow of 50 mL/min of $N_2$ to obtain metallic nickel nanoparticles. This was carried out by using a heat rate of 5 K/min from 25° C. to different temperatures, which were held for 30 min prior to cooling down.

Catalytic activity measurements were performed in a conventional quartz tubular packed bed reactor. The reactor diameter was 4 mm. The gas product composition was analyzed using an Agilent 7890A Gas Chromatograph (GC) equipped with a thermal conductivity detector (TCD) detector and using a hybrid column to separate $CO_2$ and other permanent gases.

Results and Discussion

Characterization

Two exemplary samples were prepared for this study and they were obtained by annealing fresh (non-annealed) catalyst samples (SC-25) at 450° C. (SC-450) and 700° C. (SC-700). The bulk structure of these samples was analyzed using X-ray powder diffraction and the results are shown in FIG. 1. The diffractogram of the fresh sample SC-25 indicates the presence of phyllosilicate structures [9], which are no longer detected after annealing. The peaks at 44.5°, 51.9°, and 76.4° in the diffractograms of SC-450 and SC-700 suggest the appearance of a metallic nickel phase with crystallite sizes of 3.3 and 12.3 nm, respectively. The collapse of the phyllosilicate structures was apparently accelerated by the presence of a reducing agent such as $H_2$, which is expected to be produced during the decomposition of the nickel precursor. The shoulders observed at ~36° and ~62° in both annealed samples can be attributed to changes in the structure of the phyllosilicates and appear to suggest the lack of significant differences in the bulk structure of the annealed samples.

To gain a better insight about the mechanism of formation of the nickel nanoparticles, a thermogravimetric analysis was performed on a fresh catalyst sample. The results are shown in FIG. 2A. As seen, the weight loss curve indicates that a 36.5% loss of the sample took place after annealing the sample at 450° C.; however, only a 4.5% weight loss happened when the sample was further annealed from 450° C. to 700° C. Hence, we can infer that most of the changes in the catalyst structure happened at temperatures of 450° C. and lower. In addition, the first derivative of the weight loss curve shown also in FIG. 2A suggests the catalyst samples go through different stages, starting with the elimination of residual liquids (such as ethylene glycol and water) trapped into the phyllosilicate structure (peak at 192° C.). The next step in the process appears to be the thermal decomposition of the nickel precursor (peak at 282° C.), which may be mainly located in the space between phyllosilicate layers. The stage associated with the peak at 349° C. may be attributed to the rapid collapse of the phyllosilicate structure, which appears to achieve completion as the temperature becomes higher than 500° C.

Additional information about the formation of the nickel nanoparticles was obtained through infrared spectroscopy (DRIFTS). The spectra of the samples are shown in FIG. 2B. As observed, fresh and annealed samples show significant differences which can be attributed to the absence of the functional groups existing in the structure of the Ni and Si precursors and the EG solvent. However, the annealed samples SC-450 and SC-700 seem to have only a few differences not in the fingerprint region but mostly in the functional group region. Thus, the main differences between these spectra lie in the OH stretching region where the IR spectrum of SC-450 displays a feature at 3701 cm$^{-1}$ that is not observed in any other sample. This may be the result of a strong effect caused by the appearance of nickel on the sample, for example, perhaps the formation of an intermediate species between nickel and the modified phyllosilicate structure. On the other hand, the sample SC-700 only exhibits a feature at 3737 cm$^{-1}$ that resembles that usually observed for silanol groups in silica.

The surface and sub-surface of the samples was analyzed using X-ray photoelectron spectroscopy. To do so, in addition to the original samples a new set of samples was prepared by pretreating the original ones using Ar-sputtering for several minutes. The Ni $2p_{3/2}$ and Si 2p spectra obtained for original and pretreated samples are shown in FIG. 3. The Ni $2p_{3/2}$ spectrum of the original SC-450 sample shows two peaks: one at 855.8 eV and usually assigned to Ni$^{2+}$ species (NiO octahedra in phyllosilicates), and another one at 861.7 eV, usually identified as a satellite peak. After sputtering, the sample exhibits a new peak at 852.2 eV, which is attributed to metallic nickel. Hence, the subsurface of the nickel particles appears to be metallic Ni whereas the surface seems to be at least partially oxidized. The Si 2p of the original SC-450 sample shows an asymmetric peak at 103.3 eV, which suggests the presence of more than one Si bond on the surface.

The Ni $2p_{3/2}$ spectrum of the original SC-700 sample shows peaks at 852.3, 855.8, and 860.7 eV, which can be attributed to metallic Ni, oxidized Ni, and a satellite peak, respectively. This suggests that the annealing at temperatures higher than 450° C. probably leads to the decomposition of surface species to release metallic Ni. The Si 2p XPS spectrum of this sample shows the presence of a symmetric peak at 103.4 eV, commonly attributed to Si—O bonds in silica. This indicates the disappearance of one of the Si bonds observed in the SC-450 sample, which seems to agree with the changes in the IR spectra discussed earlier. The Ar-sputtering treatment appears to produce a shift in the metallic Ni peak from 852.3 to 852.6 eV, which suggests a stronger interaction between Ni and the structure of the subsurface.

Figure 3A:
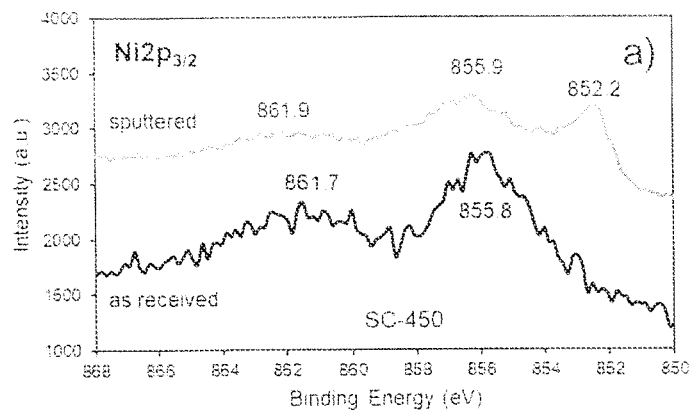
FIGS. 3A-F. XPS spectra: A and C, SC-450; B and D, SC-700; E, proposed surface structure of an SC-450 particle; F, proposed surface structure of an SC-700 particle.
Figure 3B:
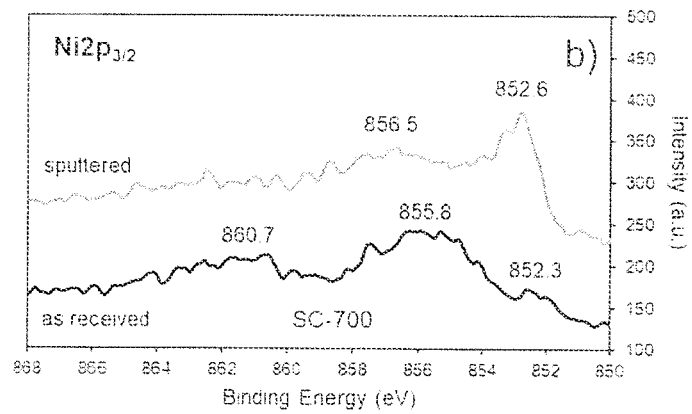
Figure 3C:
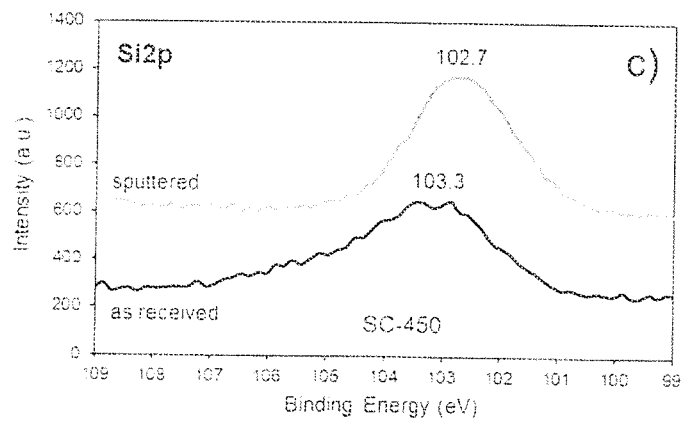
Figure 3D:
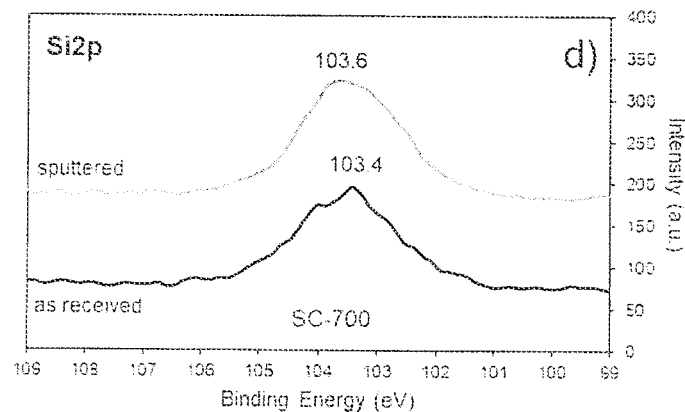
Figure 3E:
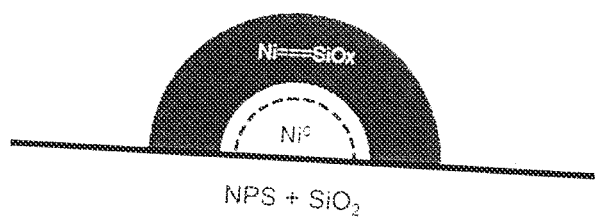
Figure 3F:
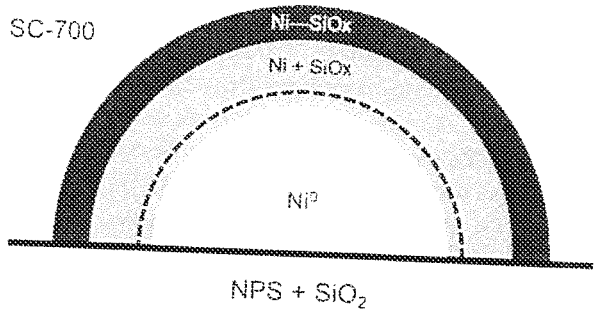

The characterization results obtained up to this point led us to elaborate a hypothetical structure for the catalyst samples, which is shown in FIGS. 3E and 3F. According to our experimental findings, the annealing at 450° C. produces small Ni nanoparticles (resulting from the decomposition of the Ni precursor trapped in the nickel-phyllosilicate (NPS) interlayer region) with a surface structure formed by Ni, Si and O, where Ni atoms strongly interact with Si—O structures (Ni=SiOx, resulting from the collapse of the NPS structure). The substrate for these Ni particles appears to be a modified or "partially collapsed" NPS structure. As the annealing temperature is raised to 700° C., the surface of the Ni particles is no longer formed by a layer with strong interactions between Ni and SiOx species and, instead, the interactions become weaker as a high migration of Si and O atoms takes place into the core of the Ni particles. Thus, the surface is then comprised of a thin outer layer of Ni and SiOx species with mild interactions (Ni—SiOx), and an inner layer with weak interactions between Ni and SiOx (Ni+SiOx). The substrate for these particles is thus a mixture of SiO$_2$ and NPS with the former predominating.

Figure 4A:
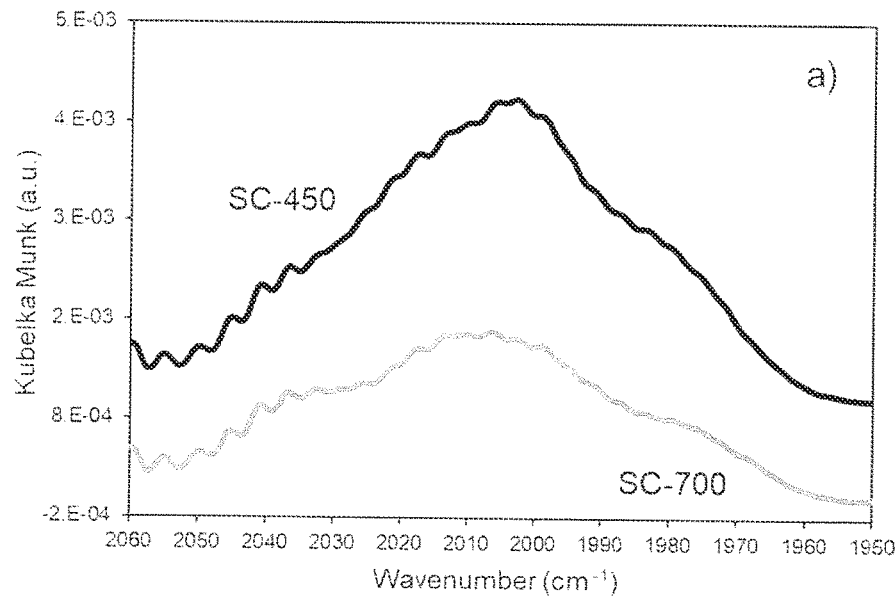
FIGS. 4A and B. DRIFTS on annealed samples @ 25° C.: A, CO, B, pyridine (LPY: Lewis acidic sites, HPY: hydrogen-bond pyridine).

The proposed surface structure described above assumes that both annealed samples contain an outer layer with properties that are expected to be similar since both are formed by Ni and Si-Ox species interacting with each other. To test this hypothesis, an additional experiment was performed to analyze the adsorption of CO using IR diffuse reflectance spectroscopy (DRIFTS). The results are shown in FIG. 4. As can be seen, both samples exhibit similar spectra with three noticeable features at around 1980, 2000, and 2025 cm$^{-1}$, which can be attributed to the linear adsorption of "metallic" nickel, adsorption on silica species, and bridged adsorption on "metallic" nickel sites, respectively. The major difference between the spectra of the annealed samples is the intensity of the signal, which appears to be higher for SC-450 compared to that of SC-700. This seems to be directly related to the total surface area of the nickel particles, which were found to be larger for the sample annealed at higher temperature, as deduced from the crystallite sizes estimated from the diffractograms (described above).

Figure 4B:
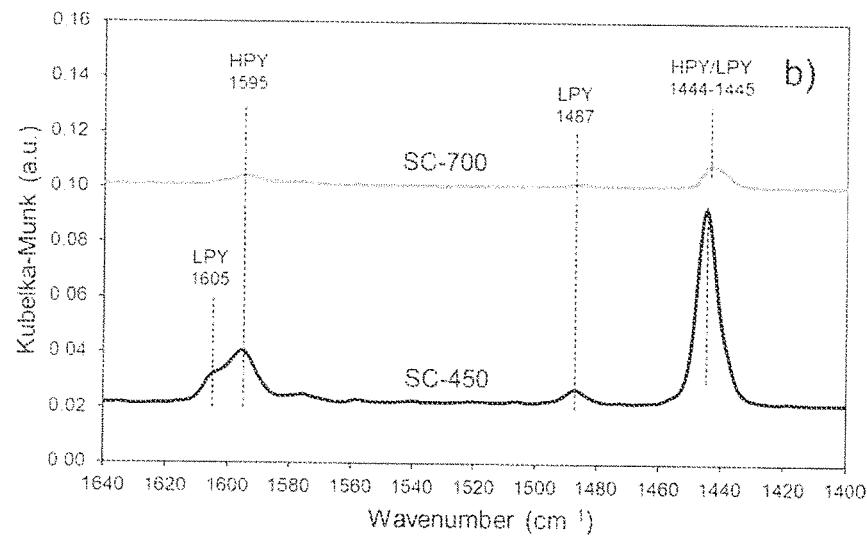

It has previously been demonstrated that the presence of Lewis acidic sites promotes the activation of methane molecules by facilitating the H abstraction, which is believed to be the first step in the mechanism of reaction of methane. On the other hand, it has been previously reported that nickel phyllosilicates possess a high concentration of Lewis acidic sites due to the presence of coordinated, unsaturated Ni atoms with the potential to generate vacancies that act as strong Lewis acidic sites. The acidity of the catalyst samples was studied using IR diffuse reflectance and pyridine as the probe molecule. FIG. 4B shows the results obtained from these tests. As can be seen, the SC-450 displays features at 1444, 1487, and 1605 cm$^{-1}$, which are typically associated with the presence of Lewis acidic sites. In addition, a peak at 1595 cm$^{-1}$, commonly attributed to hydrogen-bonded pyridine, was also observed on the spectrum of this sample, which appears to be due to the presence of the silanol groups detected in this sample using DRIFTS. The sample SC-700 shows a spectrum very different from that of SC-450 as the features assigned to acidic Lewis sites are no longer noticeable and, instead, only hydrogen-bonded pyridine is observable. The absence of acidic Lewis sites can be directly linked to the collapse of the phyllosilicate structure, which becomes almost complete at 700° C.

Catalytic Activity Assessment

Figure 5A:
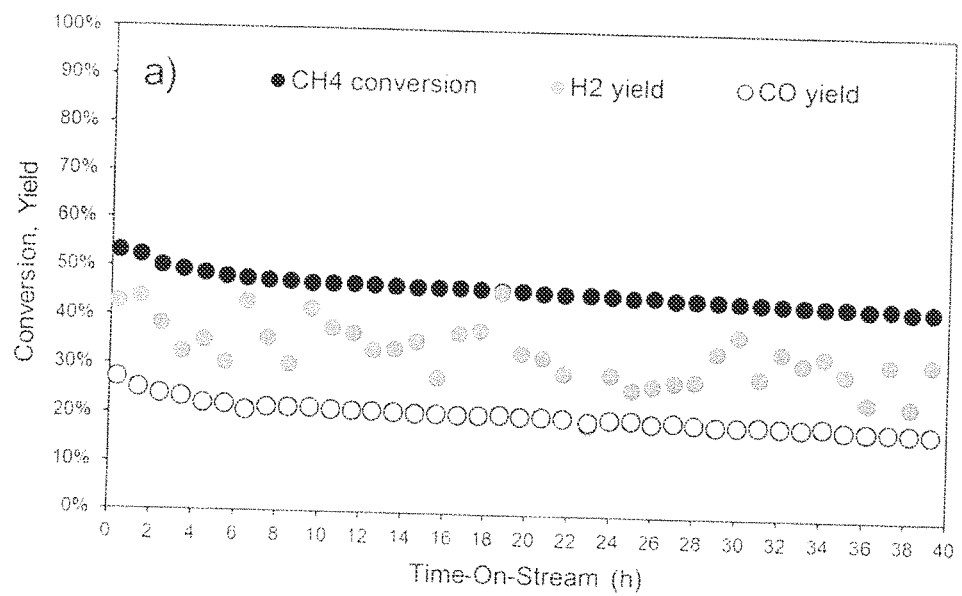
FIGS. 5A and B. A, catalytic performance of SC-450 for the CPOM @ 1 atm, 450° C., $CH_4$:air:$N_2$=5:12:20, SV=3.7 L/min-g; B, diffractograms of post-test samples FIGS. 6A and B. A, catalytic performance of SC-450 for the CPOM @ 1 atm, at the indicated decreasing temperatures; $CH_4$:air:$N_2$=5:12:20, SV=3.7 L/min-g; B, diffractogram of post-test sample.

The catalytic performance was evaluated for both annealed samples. The temperature range used for these experiments was 300-450° C. The first set of experiments was performed at 1 atm and 450° C., and its purpose was to compare the conversion and selectivity of the catalyst samples at the upper end of the temperature range. The sample SC-450 was found to be active and the performance obtained is summarized in FIG. 5A. The conversion obtained was 46% with an average H$_2$ yield of 33% and a CO yield of 21%, leading to selectivities of 72% and 46% for H$_2$ and CO, respectively. However, sample SC-700 was not able to activate methane even after 1 h on-stream.

Figure 5B:
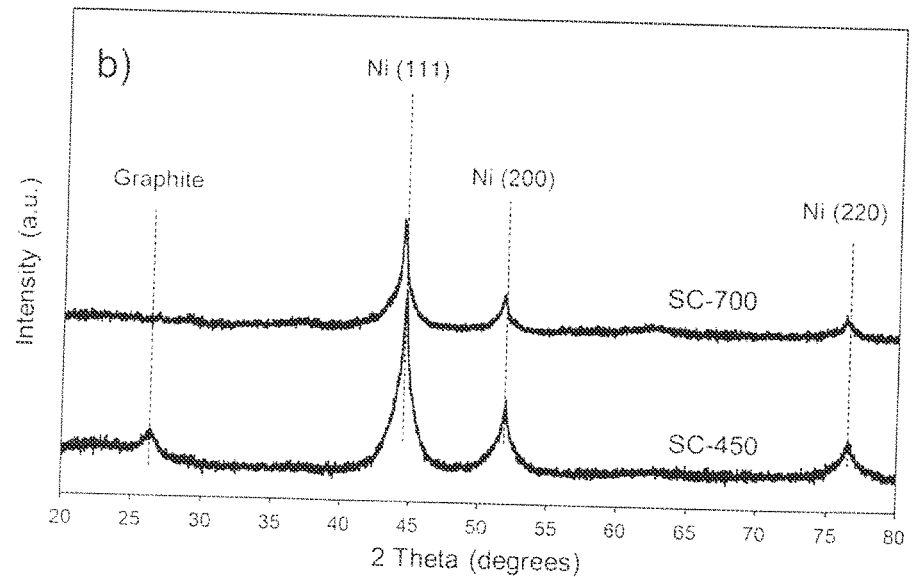

The diffractograms of the post-test samples are shown in FIG. 5B. The SC-450 sample shows only the reflections associated with metallic nickel and a small peak at ~26° associated to the formation of carbon deposits. The pattern of the SC-700 sample appears not to exhibit differences compared to that of the sample before testing, which suggests that the lack of activity displayed by this sample is not because it became rapidly oxidized but because its inability to efficiently activate CH$_4$. This could be related to the lack of acidic sites required for the activation of $CH_4$, as found during the characterization work.

Figure 6A:
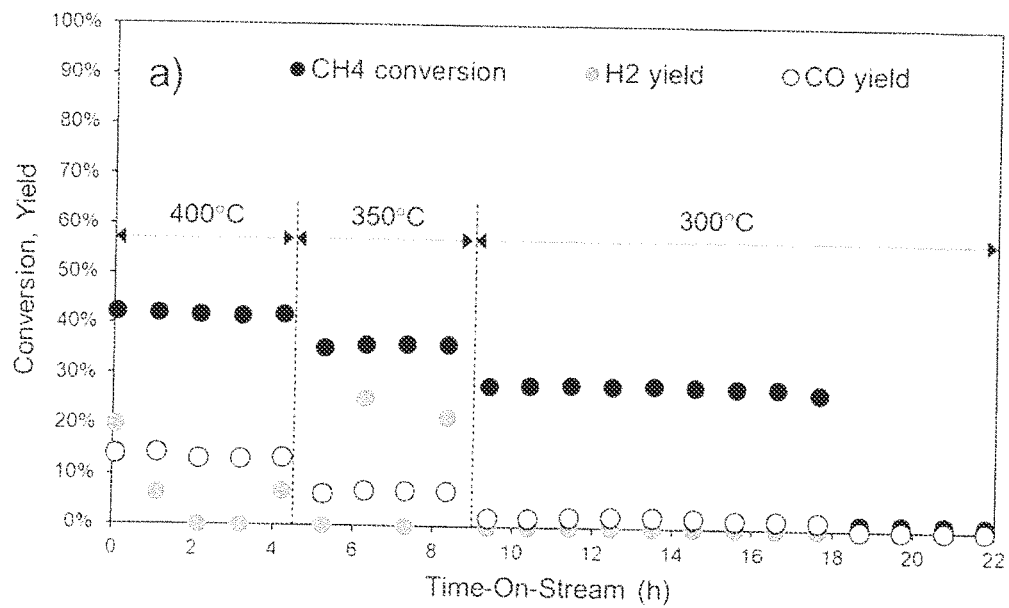
Figure 6B:
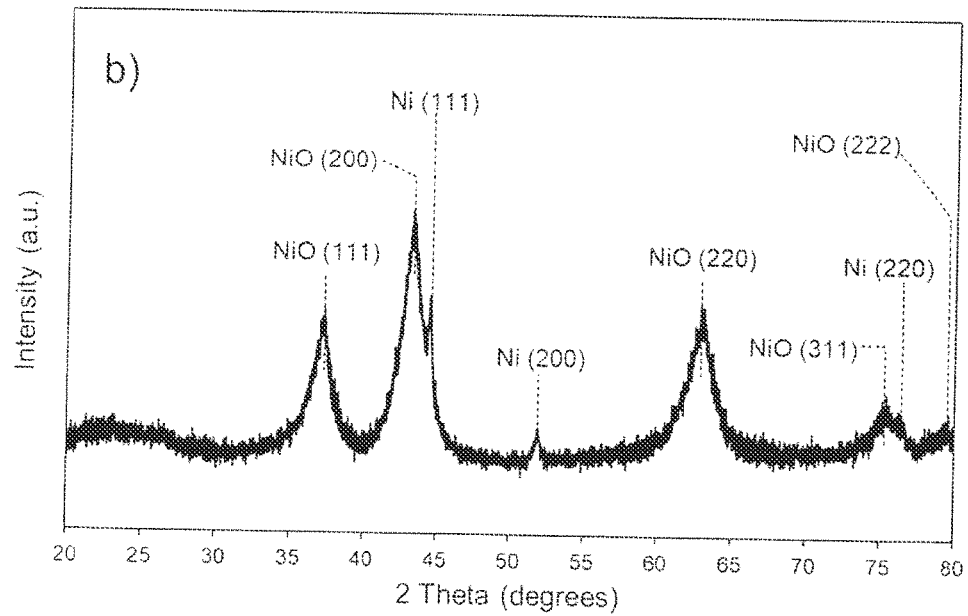

Complimentary experiments indicate that the onset temperature for the activation of methane was 400° C., that is, methane conversion is only observed when the temperature is raised to 400° C. or higher values. However, when the catalyst is already active at this temperature, the different species formed on the catalyst surface were able to hold the performance at temperatures as low as 300° C. The results of this test are shown in FIG. 6A. As can be seen, the conversions detected at 400, 350, and 300° C. were 42, 36, and 28%, respectively. Similarly, the $H_2$ yields at these temperatures were 24, 16, and 0%, respectively, while those of CO were 13, 7, and 2%, respectively. After approximately 4 h at 300° C., the sample lost activity showing only negligible methane conversion. FIG. 6B shows the diffractogram of the sample after deactivation and, as observed, the sample consisted of mostly NiO, with a small concentration of metallic nickel.

Figure 7A:
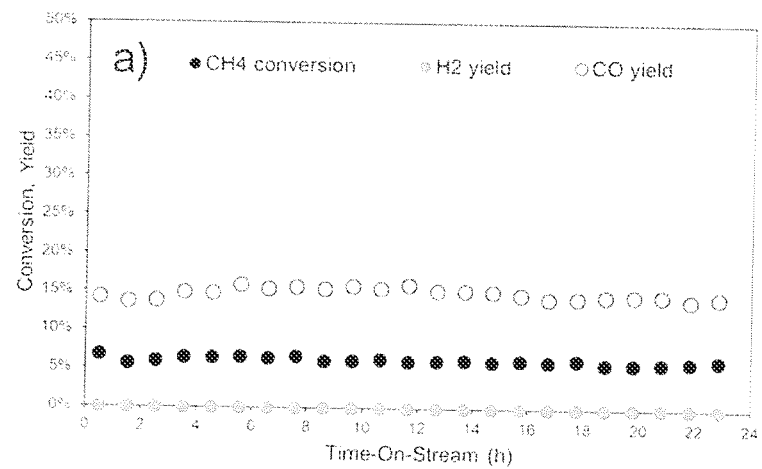
FIG. 7A-C. Catalytic performance of SC-450 for A, DRM @ 1 atm, 400° C., $CH_4$:$N_2$:$CO_2$=5:20:10, SV=3.5 L/min-g; B, SMR @ 1 atm, 400° C., $CH_4$:$N_2$:$H_2O$=5:20:5, SV=3.0 L/min-g; C, diffractogram of the post-test samples.
Figure 7B:
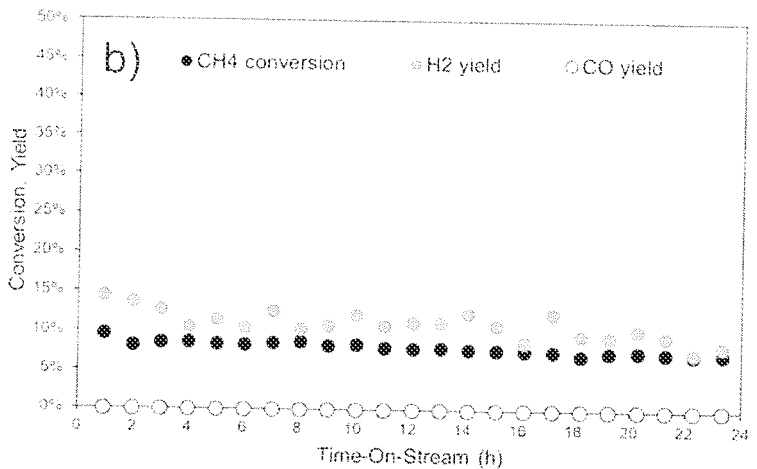
Figure 7C:
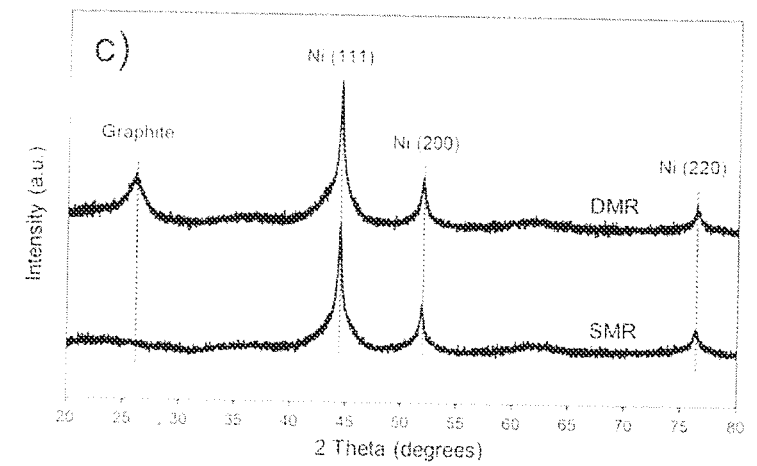

It has been previously reported by other investigators that the CPOM reaction proceeds through a sequence of steps that starts with the complete oxidation of $CH_4$ to produce $CO_2$ and $H_2O$, followed by the conversion of $CH_4$ to $H_2$ and CO using $CO_2$ and $H_2O$ as reforming agents. To investigate the feasibility of this mechanism with the catalytic materials used in the present study, samples of SC-450 were used to perform dry (DRM) and steam (SRM) reforming of $CH_4$. The results are shown in FIG. 7 and indicate that the SC-450 catalyst is active for both dry and steam reforming of $CH_4$ although the reaction is not as efficient as when $O_2$ is used as the reforming agent. Thus, $CH_4$ conversion, $H_2$ yield and CO yield were 6, 0 and 5% for DRM (FIG. 7A), respectively, and 8, 11, and 7% for SMR (FIG. 7B), respectively. The diffractograms of the post-test sample are shown in FIG. 7C and, as observed, only reflections associated to the metallic nickel phase were detected in both patterns. However, the diffractogram of the sample used for dry reforming displays a small peak at ~26°, typical of carbon deposits. Therefore, the formation of carbon during the CPOM appears to be due to the DRM process taking place during the process.

CONCLUSIONS

The catalytic activity exhibited by this novel silicon-promoted nickel catalyst appears to be the result of a synergistic effect between metallic nickel particles and acidic sites present on the surface of the phyllosilicate structure.

The metallic nickel nanoparticles seem to have a core-shell structure where the core is formed by metallic nickel and the shell a combination of nickel and silicon species with strong interactions.

The CPOM may follow the widely accepted mechanism involving full oxidation with subsequent reforming steps.

The facile synthesis of these catalytic materials makes it possible to tune the strength of the Ni—Si interactions to produce highly active catalysts with the ability to activate $CH_4$ at temperatures even lower than the ones used in the present study

REFERENCES FOR EXAMPLE 1

1. R. Conrado et al., Science, 343 (2014) 621-623.
2. R. Lipski, Gas Processing & LNG, October 2013.
3. E. Lim et al., Can J Chem Eng 94 (2016) 623-635.
4. J. Piña et al., Latin America Applied Research 36 (2006) 289-294.
5. S. Rabe et al., Appl Catal A: Gen 292 (2005) 177-188.
6. Z. Boukha et al., Appl Catal A: Gen 556 (2018) 191-203.
7. R. K. Singha et al., Appl Catal B: Env 202 (2017) 473-488.
8. Y. Zhu et al., ACS Catal 3 (2013) 2627-2639.
9. L. Yan et al., Green Chem, 19 (2017) 4600-4609.

Example 2

It is advantageous to use inexpensive oxidizing agents to carry out the oxidation of methane. Air is abundant and readily available and, thus, it is considered the most suitable oxidizing agent from an economical point of view. Although $H_2O$ and $CO_2$ can also oxidize $CH_4$, their use is practical only if it leads to an enhancement in the overall efficiency of the process. Thermodynamic calculations indicate that by increasing the amount of oxygen, a high conversion of $CH_4$ can be achieved, although with a high selectivity to $CO_2$ as the penalty. Since the reactor system is operated away from equilibrium conditions, the selectivity toward unwanted $CO_2$ production (while maintaining the high $CH_4$ conversion) should be minimized. Hence, the maximum amount of oxygen to be used can be estimated based on process safety considerations.

Figure 8:
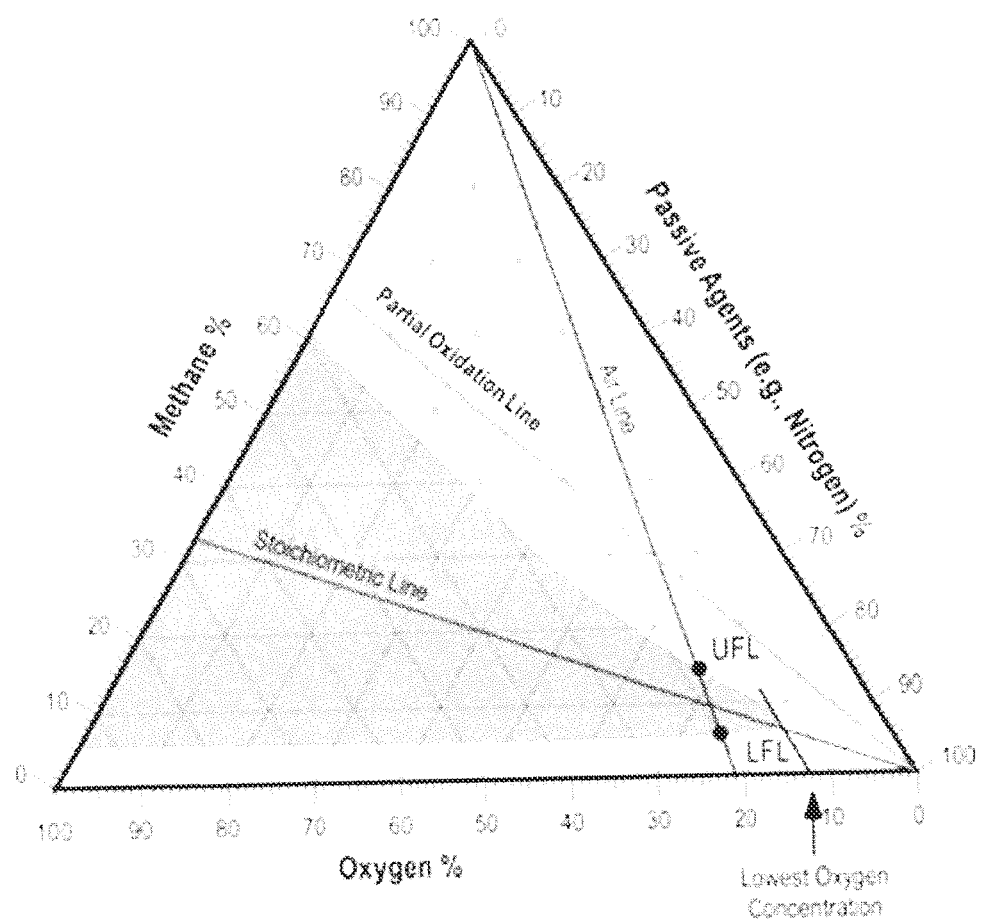
FIG. 8 shows a ternary flammability diagram for the system $CH_4$—$O_2$—$N_2$.

FIG. 8 shows a ternary flammability diagram for the system $CH_4$—$O_2$—$N_2$. As can be seen, the partial oxidation line (associated to the partial oxidation or $O_2$/C ratio of 0.5) intersects the air line outside the flammability region (i.e., the darkened area of the diagram). Thus, when using air as oxidizing agent, $O_2$/C ratios of 0.5 and lower place the reaction mixture out of the flammability region, leading the system subsequently to operate under safe working conditions.

Example 3

Synthesis and Characterization of the Catalytic Material

The chemicals used for the preparation of the catalytic materials include nickel formate dihydrate and tetraethyl orthosilicate (TEOS) as nickel (Ni) and silica ($SiO_2$) precursors, respectively. A benefit of using nickel formate dihydrate is that this precursor can be directly converted to metallic nickel upon heating under inert environments. An important aspect to be appreciated is that no hydrogen is required at any stage of the process to prepare the catalytic material.

The catalyst synthesis was carried out using a sol-gel approach, which usually involves the use of acids or bases as catalysts to accelerate the polymerization of the silicon-containing species. However, the procedure here described does not require acids or bases as catalysts and can take place in presence of the nickel formate precursor alone. The presence of the nickel formate species drives the polymerization process to produce a catalytic material with not only excellent dispersion of the metallic nickel phase, but also with a large number of acidic sites which come from the nickel-silicon sites existing on the surface of the nickel silicate phase.

Accordingly, a catalyst was prepared as follows: Ni precursor was dissolved in ethylene glycol (EG) at 90° C. to obtain a solution with a concentration of ~0.03 g/mL. Subsequently, a predetermined amount of silica precursor (TEOS) was added and the mixture stirred for 2 h at 90° C. The silica precursor was then hydrolyzed by adding a volume of nanopure water 5 times that of the TEOS. The hydrolysis was carried out at 90° C. for 5 h, after which the resulting product was left overnight to cool to room temperature without stirring. The resulting gel was subsequently centrifuged and dried (i.e. aged) at 100° C. for 5 days. Catalyst activation was conducted under $N_2$ by increasing the temperature from 25° C. to 250° C. using a heating rate of 5 K/min. After holding this temperature for 1 h, it was then raised again to 450° C. using the same heating rate.

Energy-dispersive X-ray (EDX) analysis was used to quantify the actual loading of metallic nickel in the sample. The average ratio Ni/Si was found to be 1.22, which indicates a 54 wt. % of Ni in the sample, considering Ni and $SiO_2$ as the only components of the catalyst material. XRD analysis of the activated catalyst sample showed that no nickel oxide phase was present; instead, a nickel silicate phase and metallic nickel were detected. The crystallite size for the metallic nickel phase was estimated using the Scherrer equation to be ~5 nm, and TEM imaging confirmed that the average particle size was within the range 2-5 nm. These characterization results indicated that despite the high loading of metal, a high dispersion of the active phase was obtained, likely as the result of a strong interaction between Ni and silica.

To verify this, the catalyst sample was analyzed using DRIFTS. The results showed bands typically assigned to silica although with a blue shift of bands below 2000 cm$^{-1}$. This is likely due to a strong interaction between Ni and the silica structure. A band at about 994 cm$^{-1}$ indicates the incorporation of metal ions into the silica framework, since the Si—O stretching vibration mode is perturbed by the metal ions. This interaction between Ni ions and silica in the form of Ni silicates is responsible for the high dispersion of metallic nickel on the silica support.

Analysis of Coking

One of the major issues with nickel-based catalysts is their potential deactivation due to excessive formation of carbon deposits (coke) that eventually block active sites and cause a loss of catalytic activity. Under anaerobic conditions, the activation of methane is primarily linked to the decomposition of $CH_4$ to produce C and $H_2$ according to:

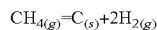

$$CH_{4(g)} = C_{(s)} + 2H_{2(g)}$$

Figure 9:
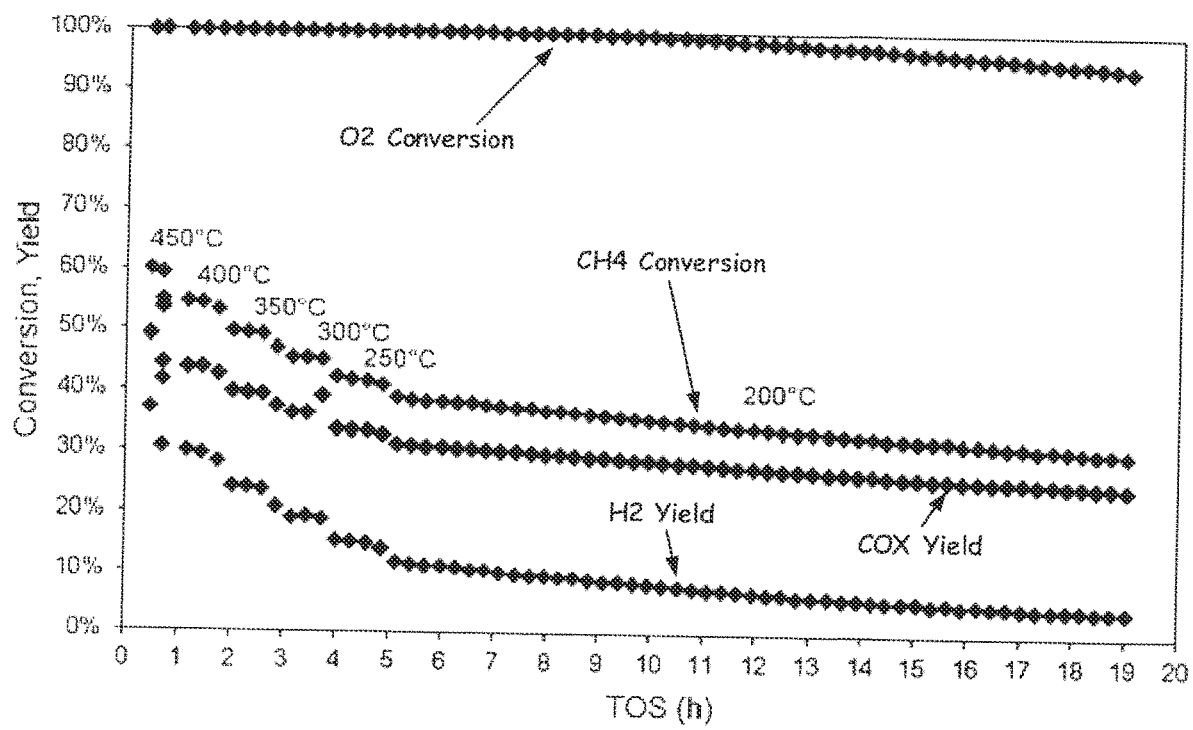
FIG. 9. Determination plot of the onset temperature for $CH_4$ decomposition.

To minimize the rates of deactivation due to coking, it is necessary to determine the onset temperature for this reaction. Operating temperatures below this point ensure that significant carbon formation will not take place, and, therefore, the catalyst will exhibit improved stability. The onset temperature for $CH_4$ decomposition on the catalyst was determined using mass spectrometry and the results shown in FIG. 9. As can be seen, a determination plot of the onset temperature for $CH_4$ decomposition shows that as the temperature is increased to values slightly above 300° C., $H_2$ evolution begins, becoming more noticeable as the temperature approaches 400° C. and higher. At 450° C., the catalyst is active enough to carry out the partial oxidation of methane as deduced from the observed conversion of $CH_4$ and the larger amount of $H_2$ produced. The data in FIG. 9 indicates that the onset temperature for $CH_4$ activation is ~310° C.

Catalytic Activity Measurements

Figure 10A:
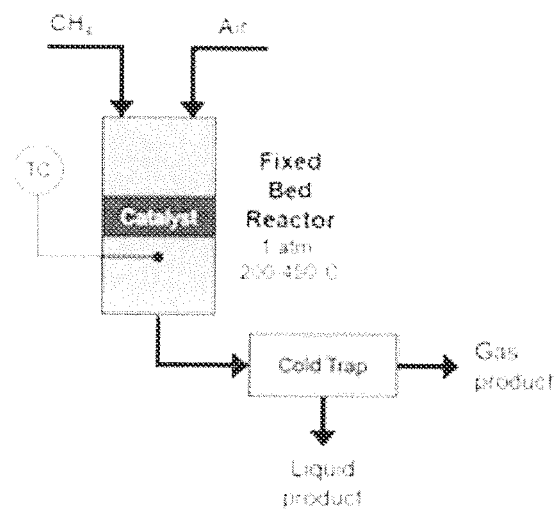
FIGS. 10A and B. Prototype of a fixed-bed reactor. A, without steam; B, with steam.
Figure 10B:
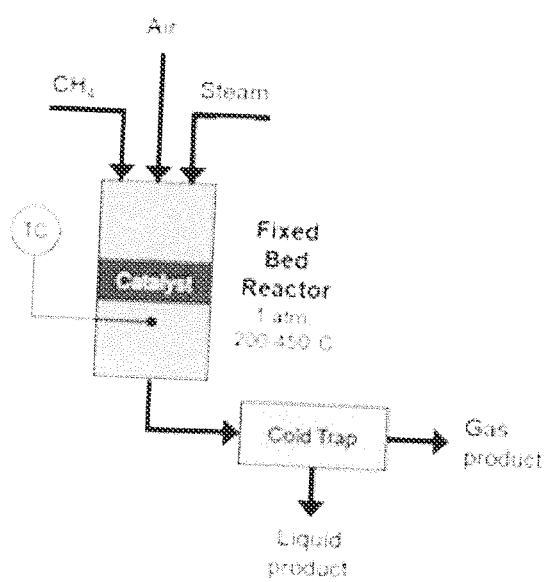

The catalytic activity was measured using a (lab-scale) fixed-bed reactor prototype which utilized a quartz tube reactor heated by an electric furnace. Two exemplary reactor systems are illustrated in FIGS. 10A and B. In FIG. 10A, the reactor is operated without steam; in FIG. 10B, the reactor is operated with steam. Experiments that were performed with steam utilized a bubbler filled with liquid water. A catalyst sample was placed in the quartz tube, supported by a quartz wool plug and placed on top of a thermocouple to measure the reactor temperature. The product stream passed through a cold trap to capture water and other condensable products. The gas product was analyzed using a gas chromatograph equipped with two columns, one filled with a 13× molecular sieve and the other with Hayesep® D packing material. The catalytic performance was evaluated in terms of methane conversion and yield of oxygenated compounds, which were identified using a detection means, such as, mass spectroscopy. The flow rate of $CH_4$ was set to 30 sccm, while the amount of air was enough to produce an $O_2/CH_{4=0.5}$. The catalyst was initially heated from room temperature to 450° C. in 30 min under 15 sccm of pure $CH_4$. At 450° C., the flow rate of $CH_4$ was adjusted to 30 sccm and air was introduced into the reactor to obtain the targeted $O_2/CH_4$ ratio. The temperature was then systematically decreased in 50° C.-steps every 45 min. Once the temperature reached 200° C., it was kept to this value for several hours.

The results in FIG. 6 showed that, even at 200° C., it was possible to activate $CH_4$ with conversions close to those predicted by thermodynamics. Thus, the equilibrium conversions at 450° C. and 250° C. were estimated as 57 and 42%, respectively, while the experimental values obtained at those temperatures were approximately 58 and 42%, respectively. At 200° C., the performance appears to decrease with time, which could be the result of the slow oxidation of the catalytic material due to the higher rates of oxidation compared to those of $CH_4$ activation. This seems to be supported by the progressive decrease of the $O_2$ conversion resulting from the decline in the number of metallic sites.

Significantly, the product distribution differs from that predicted by thermodynamics. Thus, at equilibrium conditions, the yield of $H_2$ at 250° C. was predicted to be 2% while the experimental value was 15%. Similarly, the yield of COx at equilibrium conditions was predicted to be 10% whereas the experimental value was 33%. This suggests that, unlike $CH_4$ conversion, the product distribution is kinetically controlled. Given that at temperatures of 300° C. and below the rate of carbon formation is negligible, the difference between the experimental values of conversion and yield of COx is the result of the formation of oxygenated compounds. At 450° C. this difference was ~10%, whereas at 250° C. this value was reduced to 9%, and became progressively smaller as the catalyst started to show signs of deactivation.

These results are surprising since conversion and selectivity usually follow the same trend with respect to the equilibrium values, that is, either both agree with equilibrium values or both do not agree. However, the fact that the conversion is in accordance with thermodynamic predictions and the selectivity is not suggests a reaction mechanism with a fast rate of methane activation (conversion) and a slow rate of formation of products (selectivity).

Figure 11:
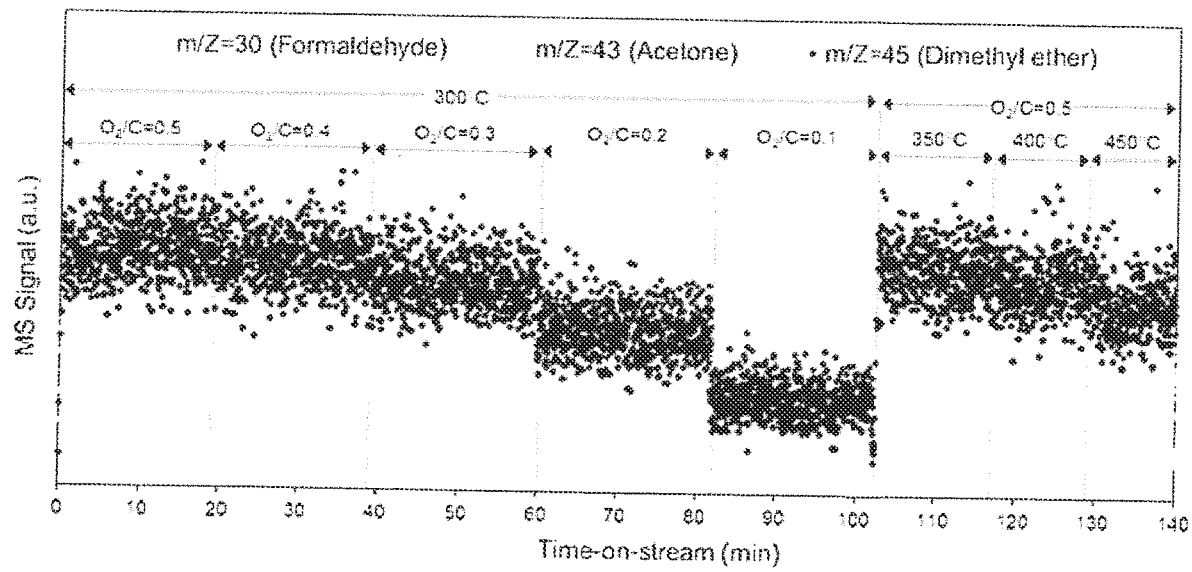
FIG. 11 shows a distribution of oxygenated compounds obtained as detected by mass spectroscopy.

FIG. 11 shows the distribution of oxygenated compounds obtained at 1 atm, $m_{cat}$=30 mg, $CH_4$=30 sccm, as detected using mass spectroscopy. The main signals correspond to the fragments m/Z=30, 43 and 45, which can be assigned to formaldehyde ($CH_2O$), acetone ($C_3H_6O$) and dimethyl ether ($C_2H_6O$), respectively. As observed, reducing the $O_2/CH_4$ ratio to values <0.4 leads to a decrease in the signals of all the oxygenated products. However, as the temperature increases from 350° C. to 450° C., the signal for formaldehyde becomes stronger whereas those of acetone and dimethyl ether decline. Hence, to maximize the production of formaldehyde the process must be operated at high temperatures (400-450° C.), whereas the production of acetone and dimethyl ether are favored by low temperatures (300-400°

C.). In addition, excessive oxidation of the catalytic material led to a significant decrease in the conversion rate and a change in the selectivity, as the only detectable oxygenated compound was methanol ($CH_4O$).

While the invention has been described in terms of its example embodiments, those skilled in the art will recognize that the invention can be practiced with modification within the spirit and scope of the appended claims. Accordingly, the present invention should not be limited to the embodiments as described above, but should further include all modifications and equivalents thereof with the spirit and scope of the description provided herein.

The invention claimed is:

1. Catalytic nanoparticles comprising
an internal core comprising metallic nickel, and
at least one external layer comprising Ni, Si, and O species, wherein the at least one external layer surrounds the internal core,
wherein the catalytic nanoparticles include both Ni metallic catalytic sites and acidic nickel-silicon catalytic sites in the at least one external layer, and
wherein the at least one external layer has a binding energy (BE) of Ni photoelectrons that is 2-3 eV greater than the BE of Ni photoelectrons of pure metallic Ni.

2. Catalytic nanoparticles comprising
an internal core comprising metallic nickel,
at least one external layer comprising Ni, Si, and O species, wherein the at least one external layer surrounds the internal core, and
an intermediate layer between the internal core and the external layer,
wherein the catalytic nanoparticles include both Ni metallic catalytic sites and acidic nickel-silicon catalytic sites in the at least one external layer,
wherein the Ni in the at least one external layer exhibits a BE of Ni photoelectrons of 0.5 eV to 2 eV greater than pure metallic Ni, and
wherein the intermediate layer comprises Ni, Si, and O species, wherein the Ni in the intermediate layer exhibits a BE of no more than 0.5 eV greater than pure metallic Ni.

* * * * *